US00PP35839P2

(12) United States Plant Patent
Hansen

(10) Patent No.: US PP35,839 P2
(45) Date of Patent: May 28, 2024

(54) ***EUCOMIS* PLANT NAMED 'PRINCESS BRIDE'**

(50) Latin Name: ***Eucomis* hybrid**
Varietal Denomination: Princess Bride

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,349

(22) Filed: Jul. 25, 2023

(51) Int. Cl.
*A01H 5/02* (2018.01)
*A01H 6/12* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP35,161 P2 * 5/2023 Hansen ..... A01H 6/12
Plt./263.1

* cited by examiner

*Primary Examiner* — Karen M Redden

(57) ABSTRACT

A new and distinct *Eucomis* plant named 'Princess Bride' with rounded-mound habit of glossy, lanceolate leaves arching with maturity. Leaves are navicular with sinuate margins, emerging moderate burgundy-colored and transitioning to chartreuse with light burgundy tinting while flowering. Freely flowering beginning in mid-summer with individual racemes lasting for about four weeks, the plants produce racemes of medium height with densely arranged flowers that open light citron yellow and transition to deep pink along tepal margins and creamy yellow in the center. 'Princess Bride' is winter-hardy to USDA zone 6 and useful as a specimen landscape plant, en masse, as a container plant, or as a cut flower.

2 Drawing Sheets

Latin name and variety denomination of the plant:
Botanical classification: *Eucomis* hybrid.
Variety denomination: 'Princess Bride'.

STATEMENT REGARDING PRIOR DISCLOSURES UNDER 37 CFR 1.77(B)(6)

The first offer for sale was made by Walters Gardens, Inc. on Jul. 28, 2022. Walters Gardens, Inc. obtained the new plant and all information relating thereto directly from the inventor. No plants of *Eucomis* 'Princess Bride' have been sold, in this country or anywhere in the world, nor has any disclosure of the new plant been made, more than one year prior to the filing date of this application, and such disclosure within one year was either derived directly or indirectly from the inventor and would be a 35 U.S.C. § 102(b) exception.

BACKGROUND AND ORIGIN OF THE PLANT

There are twelve recognized species within the genus *Eucomis* in the Asparagaceae family. The present invention relates to a new and distinct Pineapple Lily plant, *Eucomis* 'Princess Bride', hereinafter also referred to as the new plant or the cultivar name, 'Princess Bride'. *Eucomis* 'Princess Bride' was hybridized at a wholesale nursery in Zeeland, Michigan, USA on Aug. 30, 2013, as a cross between the proprietary, unnamed, selection of *Eucomis montana* (not patented) as the female or seed parent, and the proprietary, unnamed, selection of *Eucomis zambesiaca* (not patented) as the male or pollen parent. The new plant is a single seedling selection among several from the above cross identified individually by the breeder code 13-10-6 throughout the trial process. The new plant has been asexually propagated by leaf accessions and separation of the bulbs at the same nursery in Zeeland, Michigan, USA since 2017, with the resultant asexually propagated plants having retained all the same traits as the original plant.

BRIEF SUMMARY OF THE PLANT

*Eucomis* 'Princess Bride' is a distinct and new variety of Pineapple Lily. The new plant can be compared with the cultivars, 'African Night' U.S. Plant Pat. No. 31,155, 'EUW061' U.S. Plant Pat. No. 23,699, 'Reuben' (not patented), 'Safari Adventure' U.S. Plant Pat. No. 31,156, and 'Sparkling Burgundy' (not patented).

'African Night' has a taller habit and leaves that are darker burgundy when first emerging, and the flowers are more pinkish. 'EUW061' is comparable to the new variety but produces flowers that are pinkish green and the habit is less winter-hardy. 'Reuben' has flowers are that are smaller with more cranberry coloration and the foliage is more green and do not emerge with a burgundy blush. 'Safari Adventure' has a taller habit and foliage with less burgundy coloration and the flowers change color with maturity from cream to medium rosy-pink. 'Sparkling Burgundy' has darker burgundy foliage maintained into the flowering period, the racemes are deeper reddish, and the flowers open more pinkish. All of the above have a smaller topknot.

The female has darker pigment on the foliage and a shorter flower raceme with larger terminal leaves. The male parent has less upright foliage, with a shorter habit, the leaves are a lighter green color, and it has smaller terminal leaves on the top of the raceme.

*Eucomis* 'Princess Bride' is distinct from all cultivars known to the inventor in the following combined traits:

1. Bulbous winter-hardy perennial with leaves that are lanceolate, navicular, initially arching, and have a sinuate margin;
2. Foliage color is glossy above and below, and begins emerging in the spring with moderate burgundy coloring and transitions to chartreuse with a light blush at flowering;
3. Leaves are navicular with a sinuate margin;
4. Each mature bulb produces a raceme with dense flowers that open light citron yellow and transition to deep pink along tepal margins and creamy yellow in the center;
5. Winter-hardy to USDA zone 6.

BRIEF DESCRIPTION OF THE DRAWINGS

The drawings of 'Princess Bride' demonstrate the overall appearance of the new plant, including the unique traits grown in full-sun trial gardens in Zeeland, Michigan. The colors are as accurate as reasonably possible with color reproductions. Ambient light spectrum, temperature, source, and direction may cause the appearance of minor variations in color.

DETAILED BOTANICAL DESCRIPTION

Figure 1:
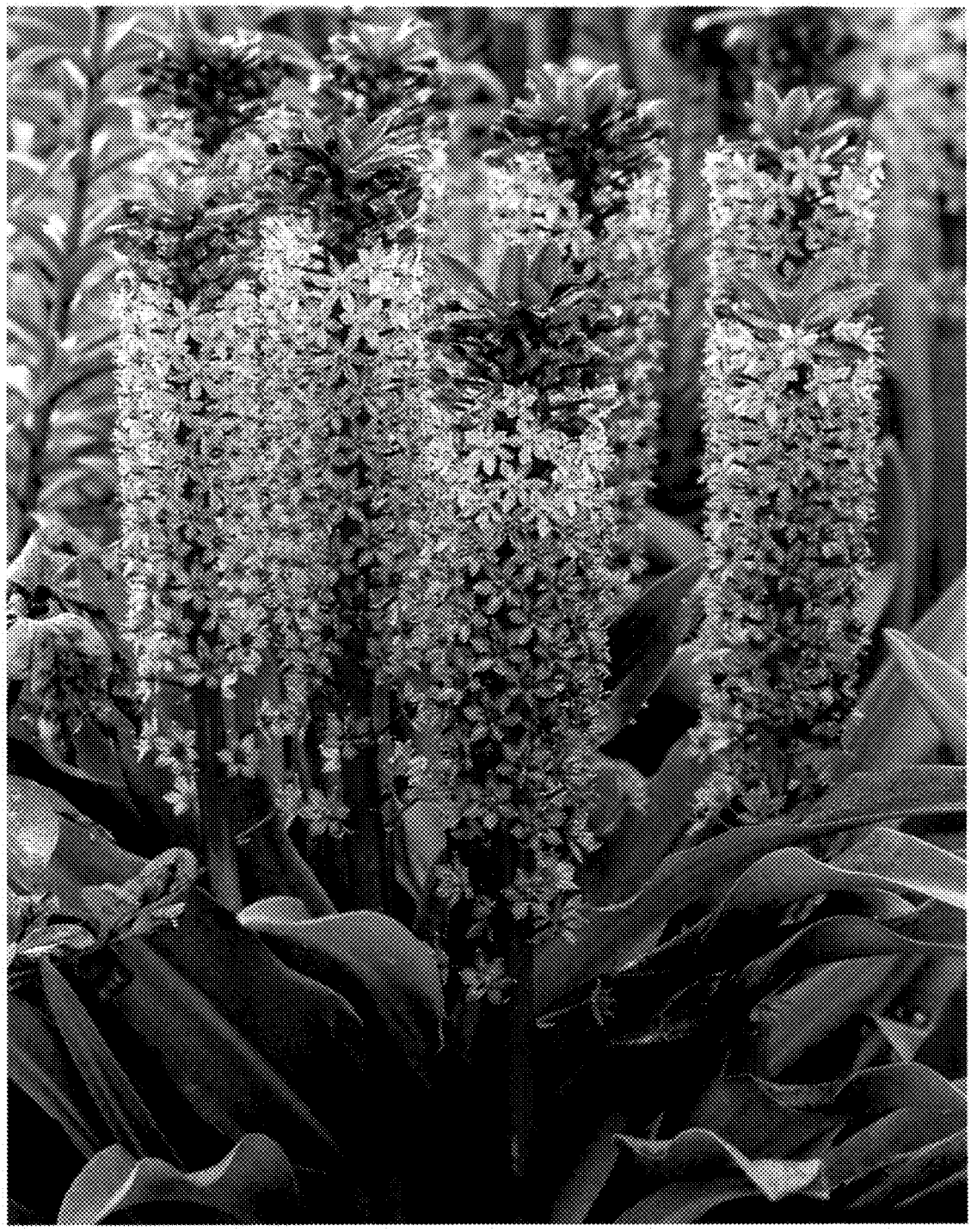
FIG. 1 shows the plant habit of an eight-year-old plant in early flower.
Figure 2:
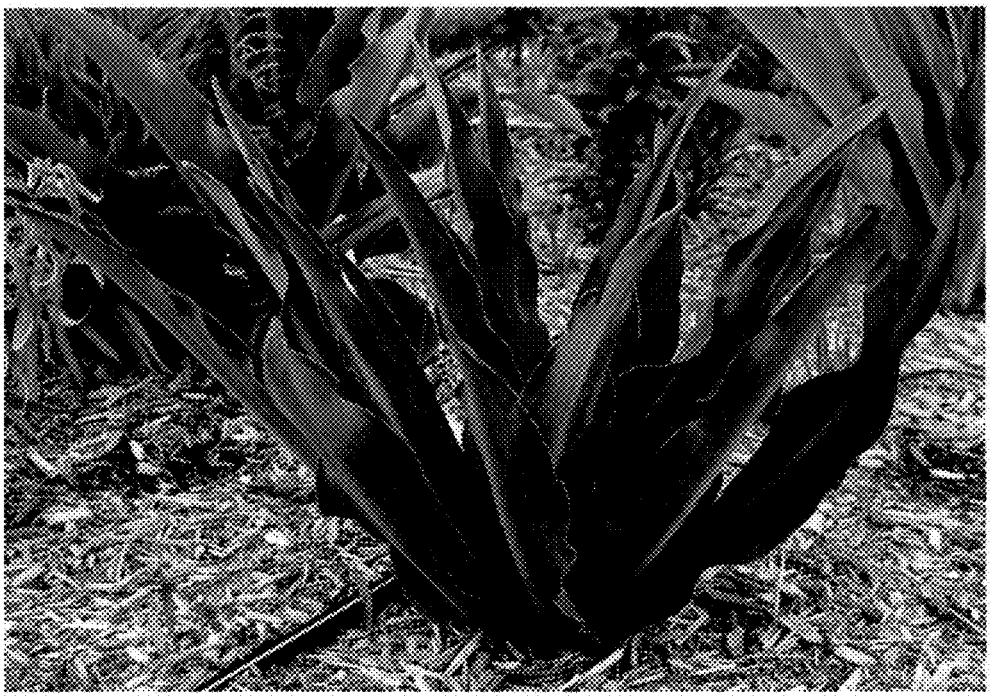
FIG. 2 shows the emerging foliage with rich burgundy coloration.
Figure 3:
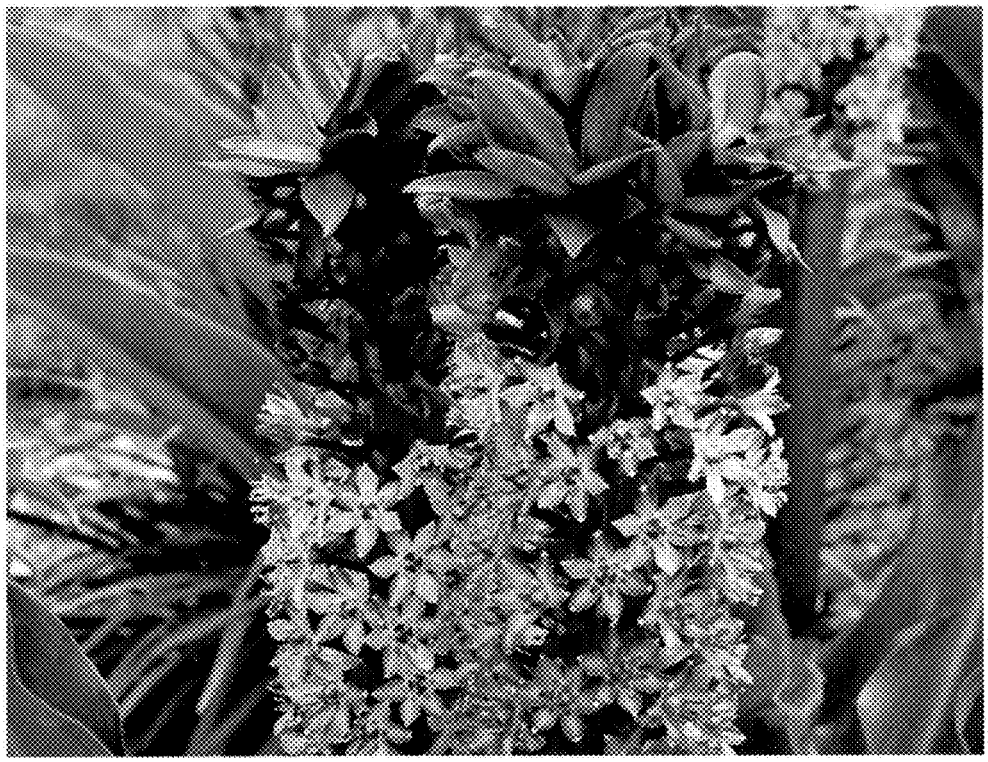
FIG. 3 shows a close-up of the flowering raceme with buds and light cream-colored flowers.

The following descriptions and color references are based on the 2015 edition of The Royal Horticultural Society Colour Chart except where common dictionary terms are used. The new plant, *Eucomis* 'Princess Bride', has not been observed under all possible environments. The phenotype may vary slightly with different environmental conditions, such as temperature, light, fertility, moisture, and maturity levels, but without any change in the genotype. The following observations and size descriptions are of a two-year-old plant in a full-sun trial garden in Zeeland, Michigan with supplemental water and fertilizer.

Botanical classification: *Eucomis* hybrid;

Parentage: A proprietary, unnamed, selection of *Eucomis montana* as the female parent, and the male parent is a proprietary, unnamed, selection of *Eucomis zambesiaca;*

Propagation: Leaf accessions, separation of the bulbs, and tissue culture of bulblets;

Time to initiate bulblets from leaf accessions: About three months during the winter growing season;

Growth rate: Moderate;

Crop time: About two growing seasons to produce flowering-size bulbs from a 25 mm liner;

Rooting habit: Normal, fleshy, lightly branching; color between RHS NN155D and RHS 158A depending on soil type and root age;

Plant shape and habit: Hardy herbaceous perennial with basal rosette of leaves emerging from a bulb producing a more or less symmetrical, rounded-mound of leaves and an upright raceme of compact flowers with a large topknot of leaves;

Plant size: Foliage height to about 36 cm above soil line to the top of the leaves and about 60 cm wide at the widest point slightly above the soil line;

Bulb: Turbinate; tunicate; about 6 cm diameter and 6.5 cm tall; color variable with portions nearest RHS NN155C and other portions between RHS 175A and RHS 175B;

Foliage description: About eleven per bulb; acaulescent arising from bulb; linear; glabrous, lustrous abaxial and adaxial; outer leaves broadly ovate, inner leaves lanceolate to linear, with narrowly acute apex and truncate clasping base; margin finely serrulate; outer blades generally flat, inner blades navicular and sinuate; slightly arcuate with maturity;

Leaf blade size: To about 46.5 cm long, 8 cm wide near base; average about 30 cm long, 6 cm wide;

Leaf blade color: Early emerging adaxial nearest RHS 146A moderately maculate with nearest RHS 187A, emerging abaxial nearest RHS 186C sides nearest RHS 187A; at flowering adaxial between RHS 147B and RHS 146B with variable light to moderate blushing of between RHS 187A to RHS 187B, mature abaxial nearest RHS 146B with faint blushing of nearest RHS 187B concentrated proximally;

Veins: With fleshy, thick, glabrous, and lustrous midrib both adaxial and abaxial; secondary veins parallel, not discernable;

Veins color: Early emerging adaxial center midrib nearest RHS N79C, emerging abaxial midrib nearest RHS N186C; mature adaxial and abaxial veins not obvious, same colors as surrounding leaf tissue;

Topknot: With twelve to twenty leaves at apex of the raceme; to about 7 cm tall and 8 cm wide; topknot leaves lanceolate with acute apex and truncate base, margin entire; cupped; leaves average about 4.5 cm long and 1.2 cm wide;

Topknot leaf color: Adaxial and abaxial center between RHS 146D and RHS 147C, adaxial and abaxial margins nearest RHS 146A with variable spotting nearest RHS 187A;

Inflorescence: Raceme; flowers radially arranged, non-secund; flowering portion about 29 cm long and 8 cm wide; racemes effective for about four weeks beginning late July in Michigan landscape, or about two to three weeks as a cut flower depending on storage conditions; remontant through summer and into early fall; about 75 to 90 flowers per raceme;

Buds one day prior to opening: Ellipsoidal with acute apex and rounded base; 10 mm long and about 7 mm diameter;

Bud color: Variable, nearest RHS 182B and between RHS 160D and RHS 161D;

Flowers: Perfect; single; regular; actinomorphic; rotate; persistent; attitude outwardly to slightly upright; about 25 mm wide and 12 mm long, decreasing distally; individually persist for about four to six weeks;

Flower fragrance: Faintly sweet;

Tepal: Six; fleshy; lanceolate; glabrous and lustrous adaxial and abaxial; margin entire; acute apex and truncate base; approximately 12 mm long and about 5 mm wide toward apex;

Tepal color: Upon opening — adaxial nearest RHS 155A, abaxial nearest RHS 155A along margin portion and center between RHS 155A and RHS 184B; mature flower — adaxial margins between RHS 186A and RHS 185C and center between RHS 160D and RHS 157D, abaxial portions exposed in bud nearest RHS 185C and portions overlapping in bud nearest RHS 157D; while developing seed — adaxial center between RHS 146D and RHS 145C, margins nearest RHS 183D; abaxial nearest RHS 146D with highlights of nearest RHS 181D;

Gynoecium: Single; tri-carpelled; 10 mm long; exserted;

*Style*.—Single; cylindrical; approximately 4 mm long, 1 mm diameter at base; color nearest 186D transitioning to RHS 183D with maturity.

*Stigma*.—Small, globose; about 0.5 mm diameter; color nearest RHS NN155D.

*Ovary*.—Superior; globose; about 5 mm long and 5 mm diameter; acute apex and truncate base; color variable, nearest RHS NN155D and between RHS 186B and RHS 186A.

Androecium:

*Filaments*.—Typically, six; adnate to inner corolla and connate in basal 3 mm; cylindrical distally and applanate proximally; approximately 9 mm long and 2 mm wide at base; color initially between RHS 157A and RHS 160D, transitioning to nearest RHS 183B and nearest RHS 187B and with seed development nearest RHS 146A proximally and RHS 183B distally.

*Anthers*.—Oblong; dorsifixed; longitudinal; about 4 mm long and 2 mm wide; color nearest RHS 11D.

*Pollen*.—Abundant; less than 0.1 mm; color nearest RHS 16D.

Peduncle: Terete; usually one per mature division and eight per plant; lustrous, glabrous; upwardly; to about 48 cm long, and about 16 mm in diameter at base; average about 44 cm long and 13 mm diameter;

Peduncle color: Where exposed to sun nearest RHS N186C, where shaded nearest RHS 146D;

Pedicel: Glabrous; lustrous; cylindrical; slightly upwardly; approximately 24 mm long and 2 mm diameter;

Pedicel color: Nearest N186C and nearest RHS 146D where protected from strong light;

Foliar bract: Each flower subtended by a single bract; deltoid; acute apex; truncate base; entire margin; to about 12 mm long and 5 mm across base; adaxial and abaxial color between RHS 186D and RHS NN155D in center with margins nearest RHS N186D;

Fruit: Tri-lobed; with acute apex and truncate base; tri-valved dehiscent capsule; about 12 mm long and 16 mm across; color as maturing striped with nearest N186D and nearest RHS NN155A;

Seed: Ellipsoidal; about 3.5 mm long and 2.5 mm wide; color nearest RHS 202A;

Disease and pest tolerance and resistance: The new plant has not shown any resistance to pests and diseases common to Pineapple Lilies. Other disease resistance is typical of that of other *Eucomis*.

Growth: The plant grows best and shows the best coloration with plenty of moisture, adequate drainage, and full sun. Winter hardiness has been tested in USDA zone 6 with excellent survivability.

It is claimed:

1. A new and distinct ornamental *Eucomis* plant named 'Princess Bride' as herein described and illustrated.

* * * * *